United States Patent [19]

Hesse

[11] Patent Number: 4,731,068
[45] Date of Patent: Mar. 15, 1988

[54] NON-RELOADABLE SYRINGE

[76] Inventor: John E. Hesse, 827 Stetson St., Moss Beach, Calif. 94038

[21] Appl. No.: 45,867

[22] Filed: May 1, 1987

[51] Int. Cl.$^4$ .............................................. A61M 5/00
[52] U.S. Cl. ................................... 604/110; 604/218
[58] Field of Search ....................... 604/110, 111, 218

[56] References Cited

U.S. PATENT DOCUMENTS

| | | |
|---|---|---|
| 325,132 | 8/1885 | Tagliabue . |
| 1,571,268 | 2/1926 | Hein . |
| 1,834,713 | 12/1931 | Kahn . |
| 2,688,325 | 9/1954 | Lockhart . |
| 3,478,937 | 11/1969 | Solowey . |
| 4,144,885 | 3/1979 | Stait . |
| 4,233,975 | 11/1980 | Yerman .............................. 604/110 |
| 4,252,118 | 2/1981 | Richard et al. ...................... 604/110 |
| 4,333,457 | 6/1982 | Margulies . |
| 4,367,738 | 1/1983 | Legendre . |
| 4,493,703 | 1/1985 | Butterfield . |
| 4,571,242 | 2/1986 | Klein . |

Primary Examiner—John D. Yasko
Attorney, Agent, or Firm—Flehr, Hohbach, Test, Albritton & Herbert

[57] ABSTRACT

In general a non-reloadable syringe has been provided wherein the plunger unit thereof is permitted to be withdrawn for purposes of loading the syringe and permitted to be urged forwardly to discharge the contents of the syringe. However, means are provided whereby subsequent retraction of the plunger assembly is inhibited to prevent further loading and use of the syringe.

7 Claims, 31 Drawing Figures

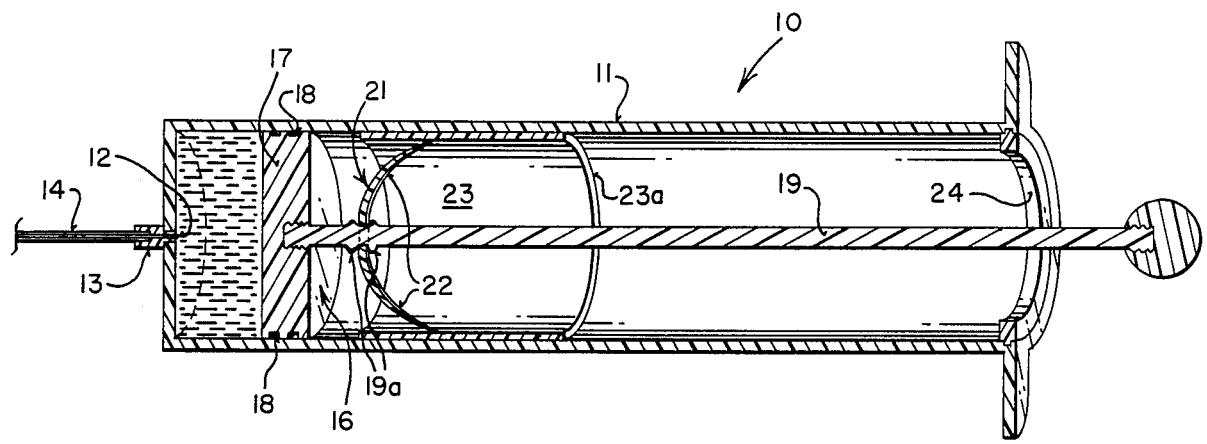
FIG_1
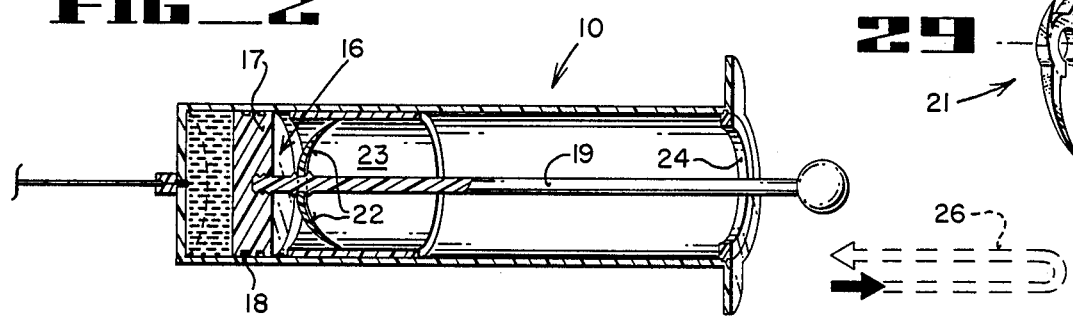
FIG_2  FIG_29
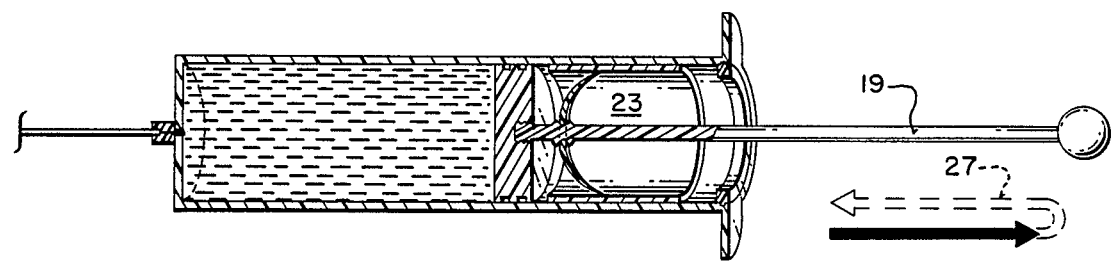
FIG_3
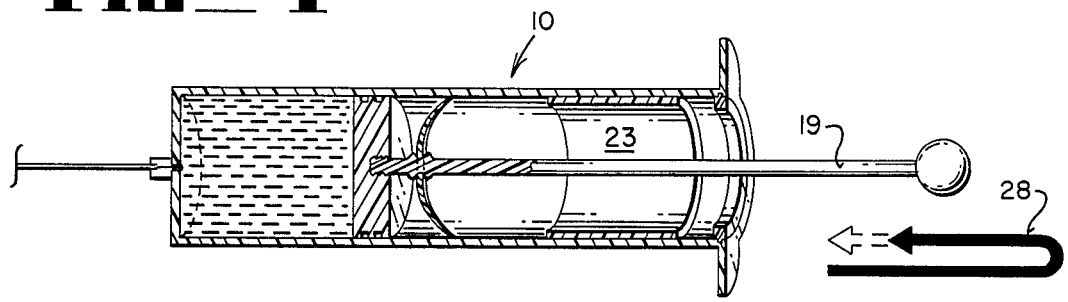
FIG_4

FIG_5
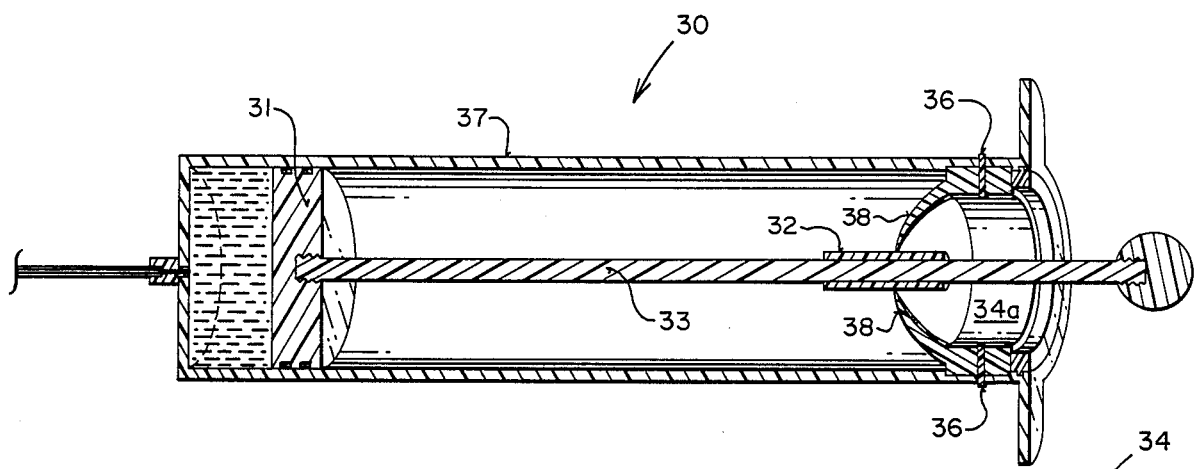
FIG_6
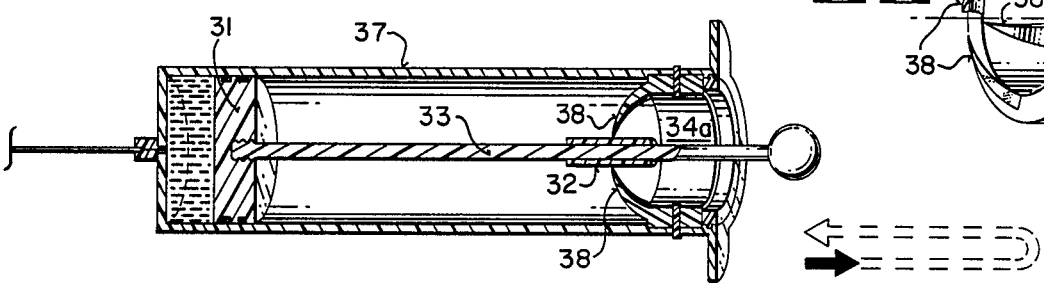
FIG_30
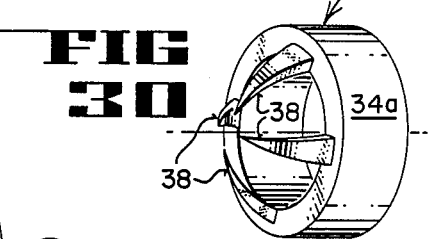
FIG_7
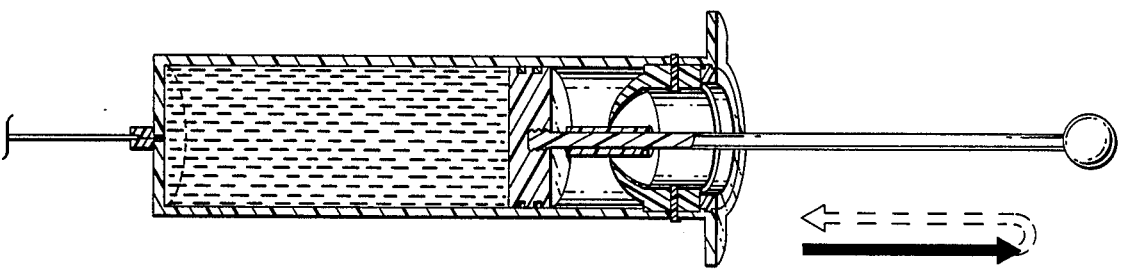
FIG_8
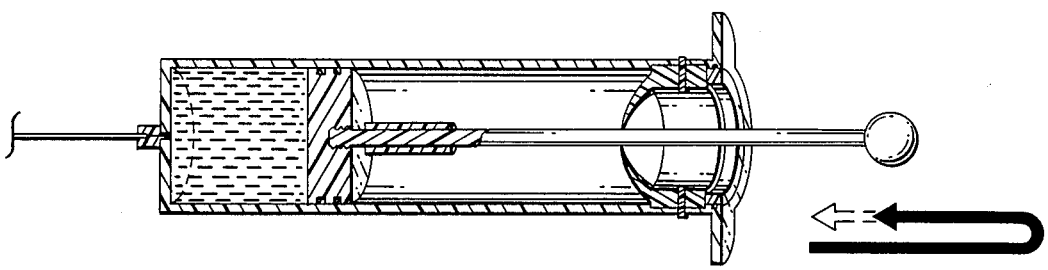

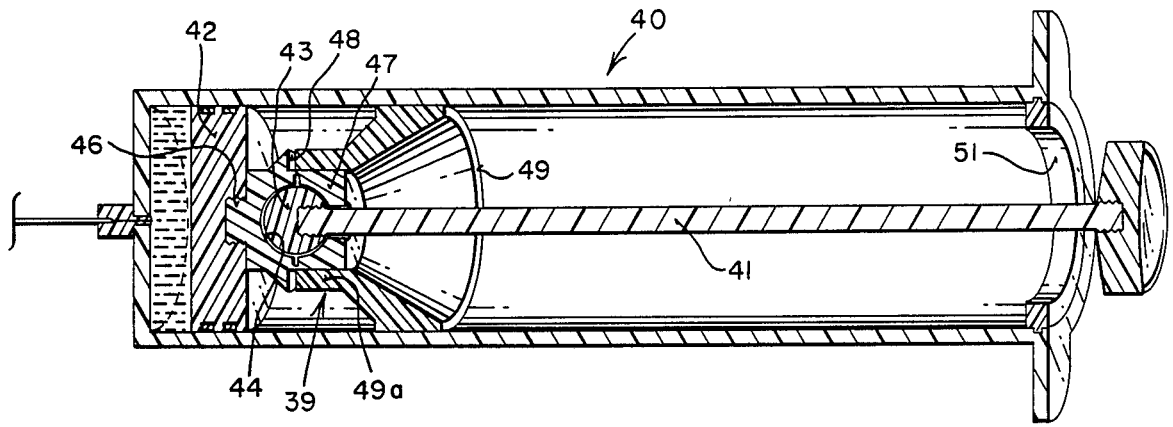
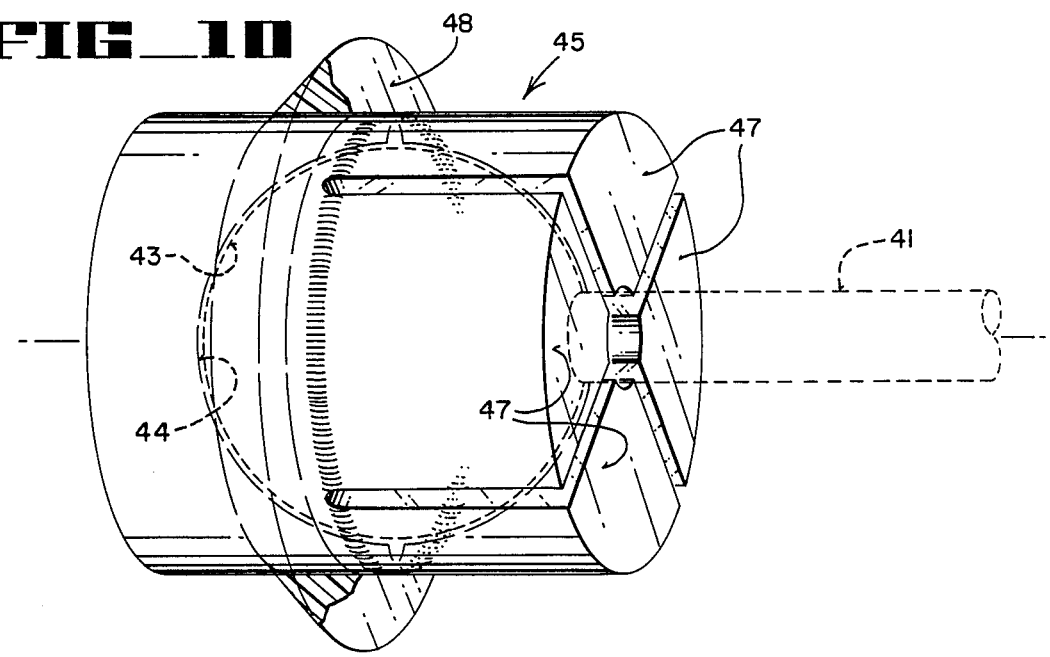
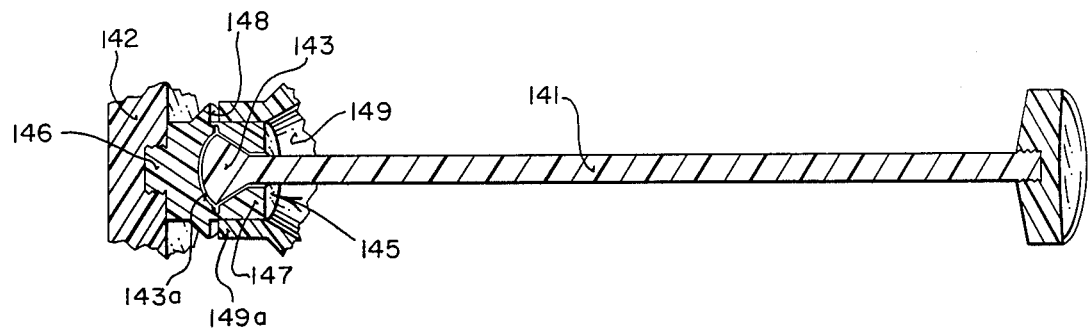

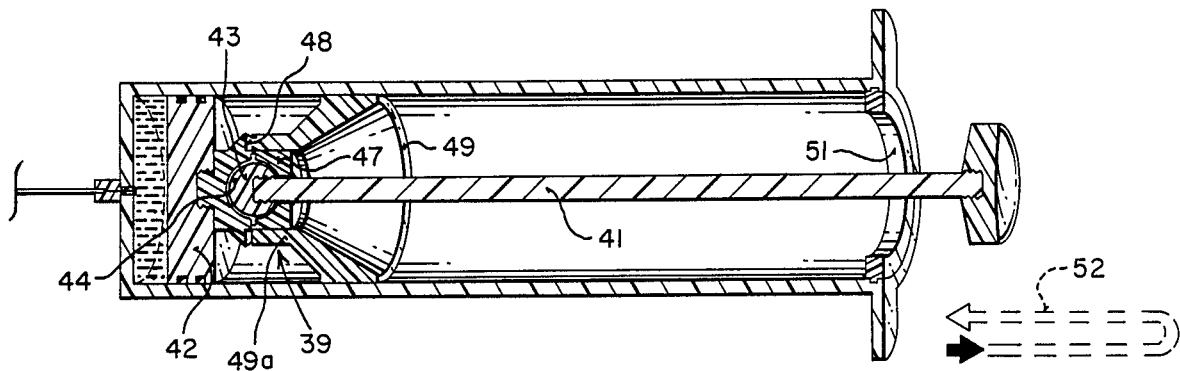
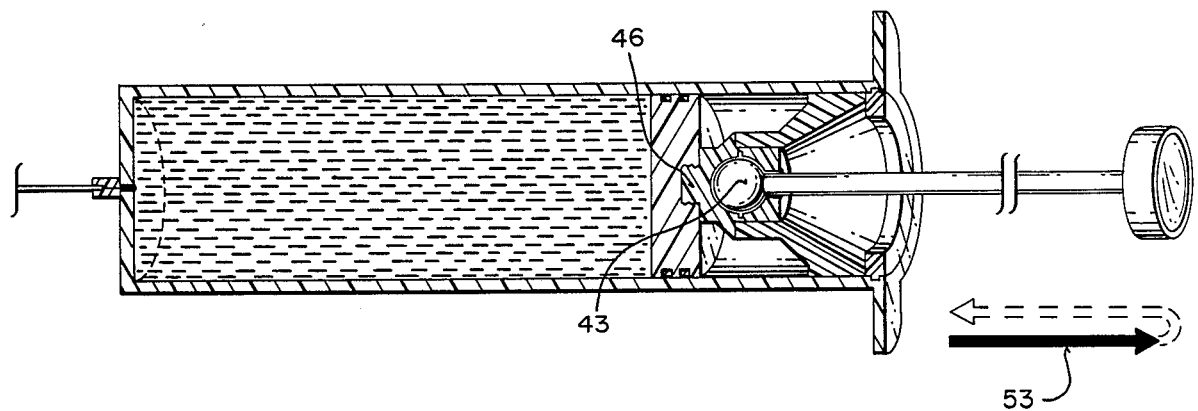
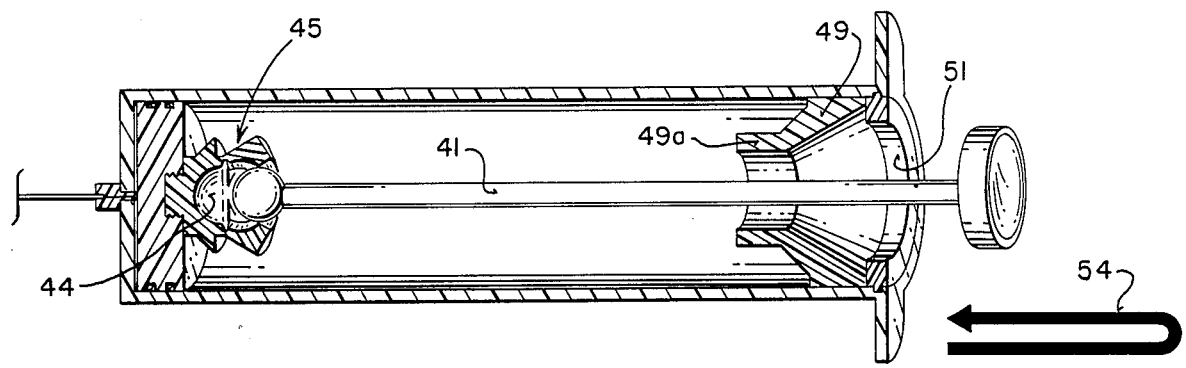

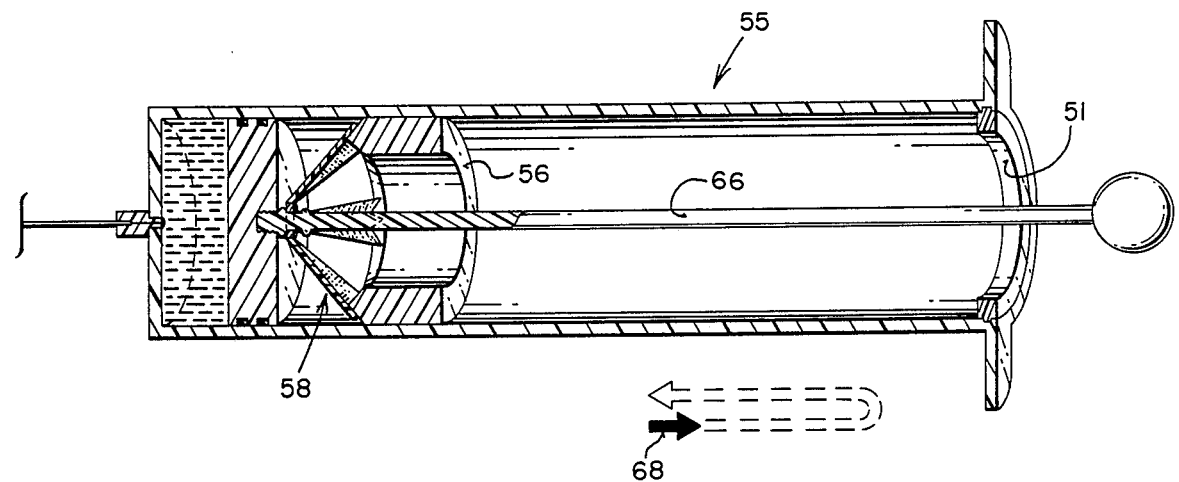
FIG_14
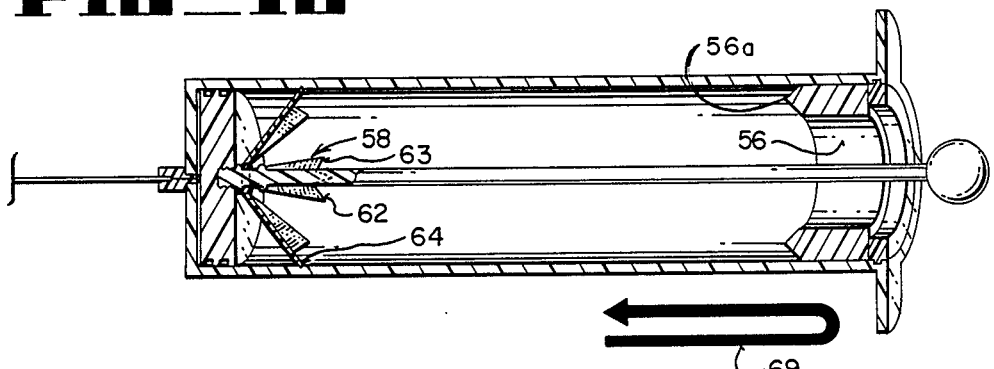
FIG_15
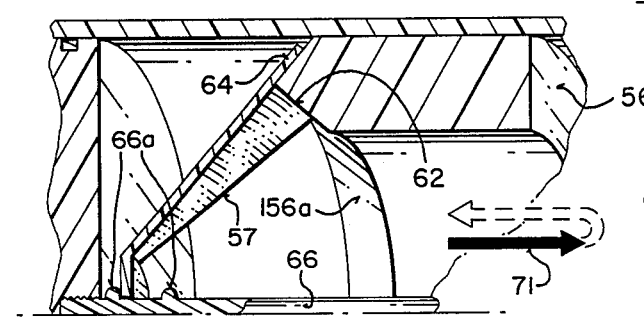
FIG_16
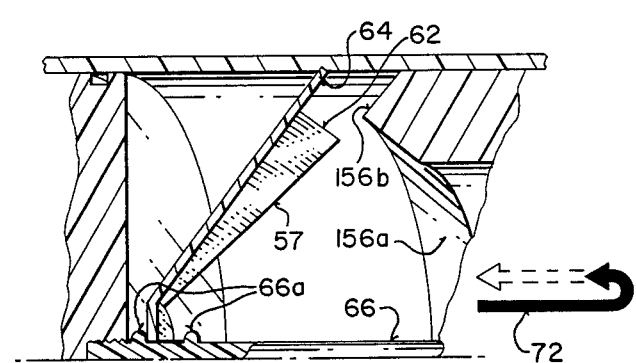
FIG_17
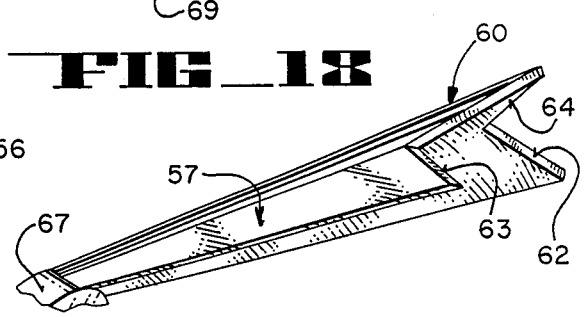
FIG_18
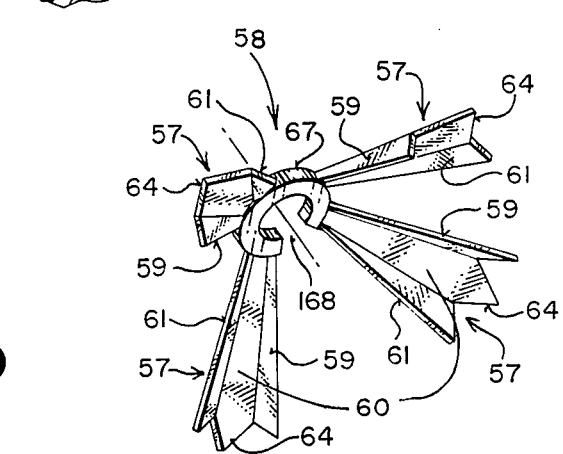
FIG_19

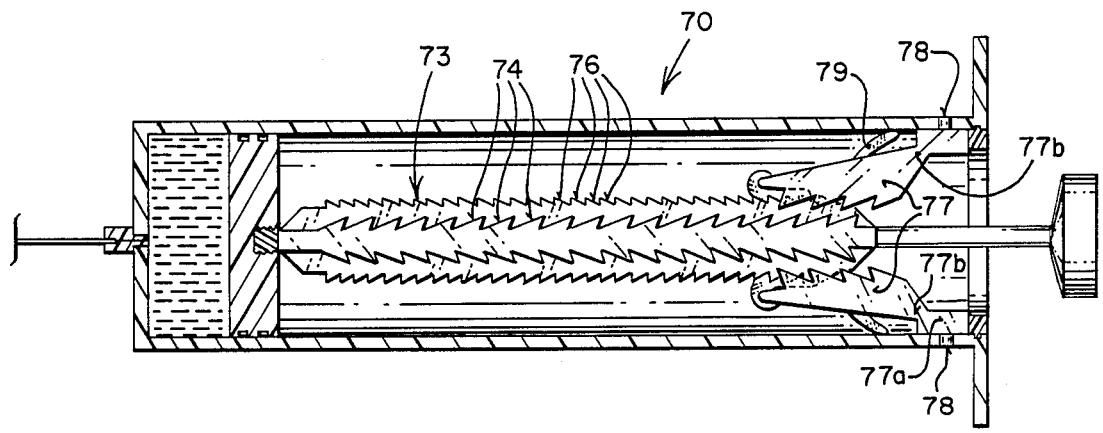
FIG_20
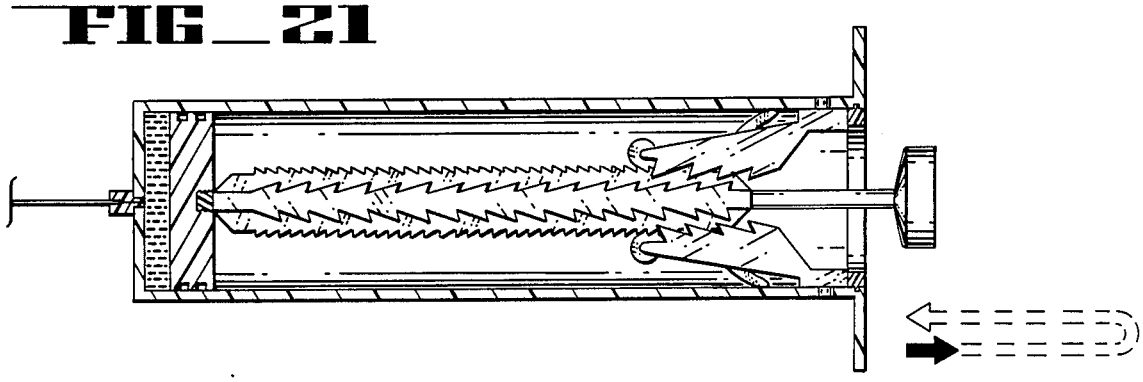
FIG_21
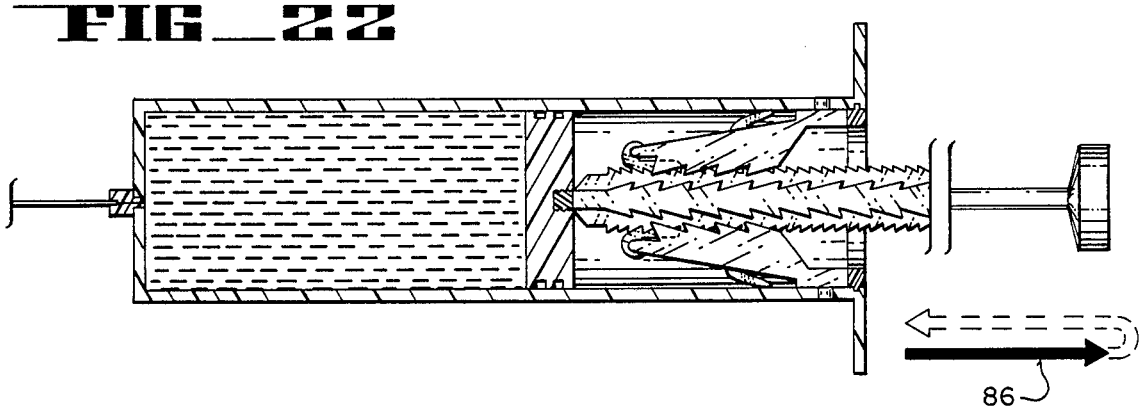
FIG_22
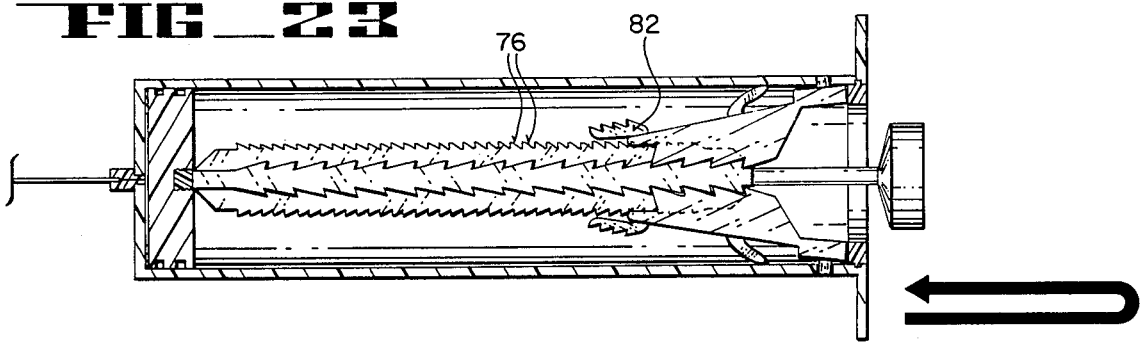
FIG_23

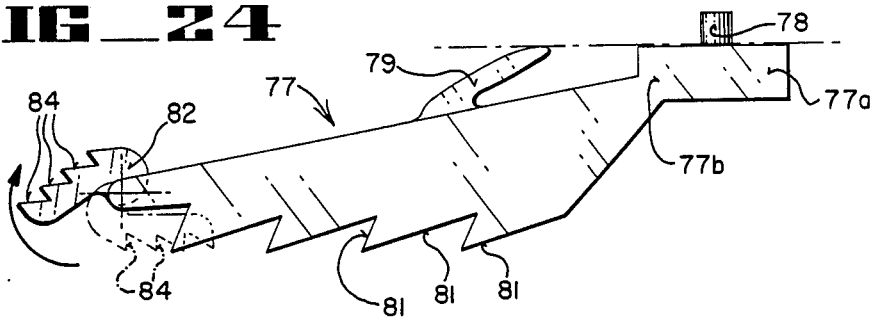
FIG_24
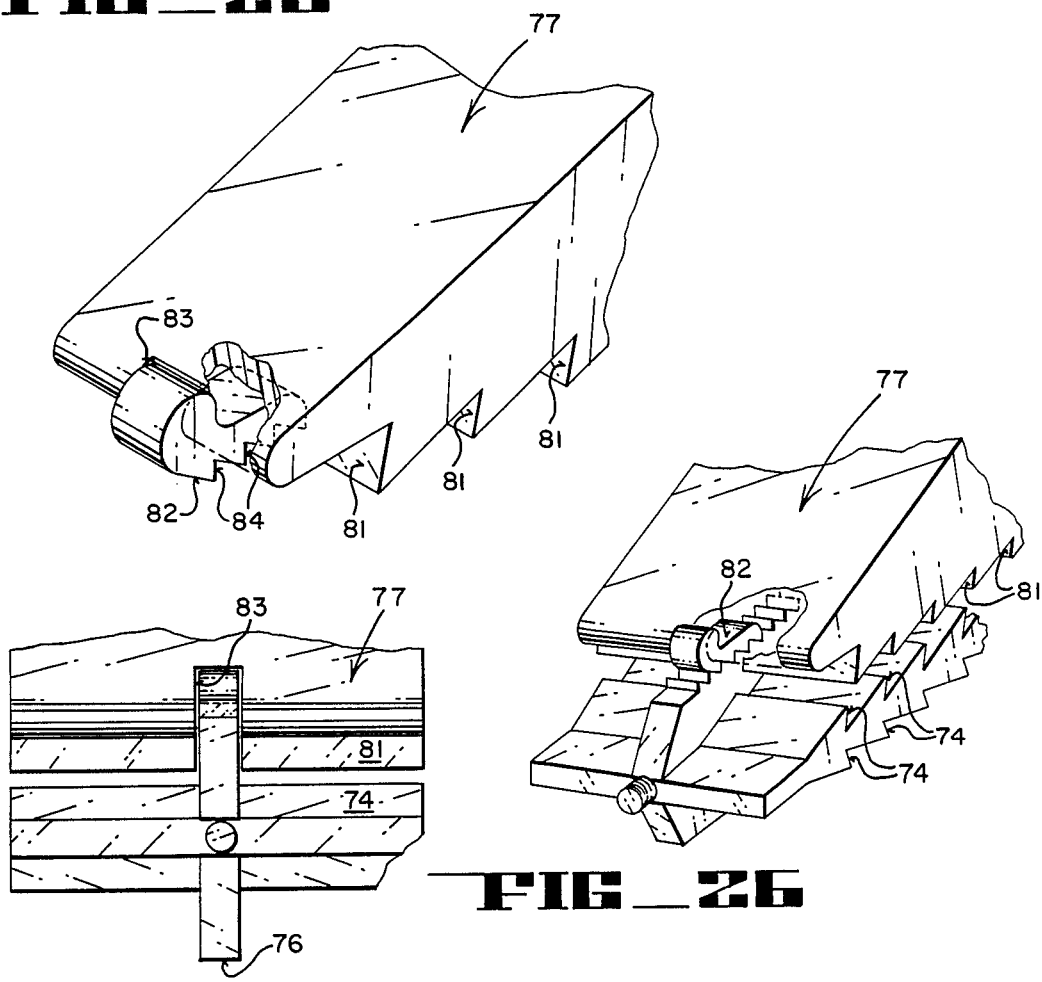
FIG_25
FIG_26
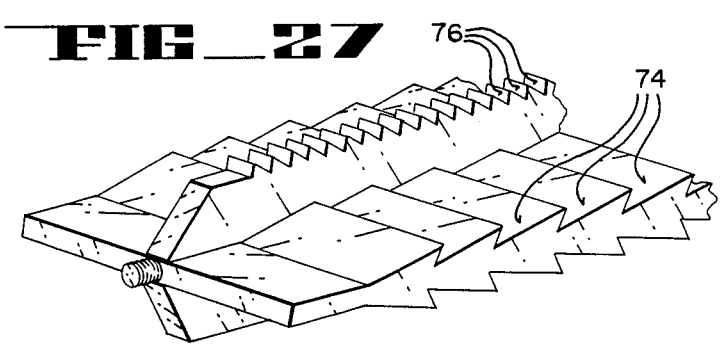
FIG_27
FIG_28

NON-RELOADABLE SYRINGE

This invention pertains to a syringe assembly and more particularly to a syringe assembly which is incapable of being reloaded after it has been loaded and discharged once.

It has been observed that serious diseases can be spread by the usage among several people of a common syringe.

For example, the serious illness referred to as Acquired Immune Deficiency Syndrome, or AIDS, is known to be communicated by sharing of a syringe among several people. It is believed that by making it difficult, if not impossible, to reload a given syringe, the foregoing practice can possibly be limited. Accordingly, as disclosed herein, a number of embodiments of a syringe assembly have been disclosed containing means which serve to inhibit recharging of the syringe with material to be dispensed.

SUMMARY OF THE INVENTION AND OBJECTS

In general, a non-reloadable syringe of a type to be charged with fluid material and for discharging said material via a given end of the syringe includes first and second members such as a barrel and a plunger assembly disposed therein arranged in a manner whereby one of said members is coaxially spaced with respect to the other member. A first of the members is axially movable relative to the other between advanced and retracted positions for loading and discharging the syringe. Sliding means axially movable with respect to a given one of the members engages a plurality of pointed prongs carried by the other one of the members. The prongs extend radially into engagement with the sliding means to maintain the prongs disengaged from the given one of the members during retraction of the first of said members. The prongs disengage from the sliding means for engagement with the second of the members in response to movement of the first of the members to its advanced position for discharging fluid material from the syringe.

In general, it is an object of the present invention to provide a syringe assembly which can be loaded and unloaded in the conventional manner of retracting and advancing a plunger within the syringe but which cannot thereafter be reloaded.

It is a further object of the invention to provide a syringe assembly of a type capable of being used in a conventional manner but characterized by means for inhibiting its use more than once.

It is yet another object of the invention to provide a syringe assembly characterized by means for inhibiting a plurality of retractions of the piston therein so as to permit an initial loading but not a reloading of the syringe.

It is yet another object of the invention to provide a syringe assembly of a type tending to discourage the sharing of a syringe among a plurality of people and in this way to minimize the likelihood of transfer of disease from one to another.

The foregoing and other objects of the invention will become more readily evident from the following detailed description of preferred embodiments when considered in conjunction with the drawings.

BRIEF DESCRIPTION OF THE DRAWINGS

FIG. 1 shows a single plane perspective view in centerline section and in enlarged detail of a syringe assembly according to the invention;

FIGS. 2, 3 and 4 each show a single plane perspective view in centerline section of the syringe of FIG. 1 in various stages of operation;

FIG. 5 shows a single plane perspective view in centerline section in enlarged detail of a syringe assembly according to another embodiment of the invention;

FIGS. 6, 7 and 8 each show a single plane perspective view in centerline section of the syringe assembly of FIG. 5 in various stages of operation for explanation;

FIG. 9 shows a single plane perspective view in centerline section of a syringe assembly according to another embodiment of the invention;

FIG. 10 shows in enlarged detail a single plane perspective view of a ball-retaining coupling assembly of FIG. 9;

FIG. 10A shows another embodiment of the retaining assembly shown in FIG. 10 according to another embodiment of the invention;

FIGS. 11, 12 and 13 each show a single plane perspective view in centerline section of the embodiment shown in FIG. 9 according to various stages of operation;

FIG. 14 shows a single plane perspective view in centerline section of a syringe according to another embodiment of the invention;

FIG. 15 shows a single plane perspective centerline section view of the embodiment shown in FIG. 14 according to a subsequent stage of operation;

FIGS. 16 and 17 each show single plane centerline section views in enlarged detail showing the interrelationship of portions of the embodiment shown in FIG. 14 in two different stages of operation;

FIG. 18 shows in a perspective view in enlarged detail of a single prong portion of the spider utilized in the embodiment shown in FIG. 14;

FIG. 19 shows a perspective view of the spider element employed in the embodiment of FIG. 14;

FIG. 20 shows an enlarged centerline section view of a syringe assembly according to another embodiment of the invention;

FIGS. 21, 22, 23 show the syringe assembly of the embodiment shown in FIG. 20 in various stages of operation;

FIG. 24 shows in enlarged detail a side elevation view of a dog element employed in the embodiment of FIG. 20;

FIG. 25 shows a perspective view in further enlarged detail of the leading end of the dog element as shown in FIG. 24;

FIG. 26 shows in enlarged detail a perspective view with portions broken away for clarity of the leading end of the dog unit disposed in cooperation with a portion of the drive rod assembly shown in the embodiment in FIG. 20;

FIG. 27 shows a front elevation view of the end of the drive rod with the dog element disposed thereabove;

FIG. 28 shows an enlarged perspective view of a portion of the drive rod employed in the embodiment of FIG. 20;

FIG. 29 shows a four-legged spider element as employed in the embodiment shown in FIGS. 1 through 4; and FIG. 30 shows a perspective view of a spider element as used in the embodiment of FIG. 5.

DETAILED DESCRIPTION OF PREFERRED EMBODIMENTS

A syringe assembly 10 generally comprises an elongated right cylindrical barrel 11 formed with a small opening 12 at one end of barrel 11 for passing fluid into and out of barrel 11. Means for supporting a hypodermic needle 14 for passing fluid into and out of the barrel 11 includes a boss element 13 protruding from one end of barrel 11.

Means forming a plunger assembly for loading and discharging fluids into and out of barrel 11 of syringe 10 includes a piston 17 snugly fitted within the right cylindrical interior of barrel 11 and provided with resilient sealing rings 18 therearound. Means for moving piston 17 between advanced and retracted positions includes a drive rod 19 formed with threads on one end to threadedly engage corresponding threads formed in piston 17.

As noted above, syringe assembly 10 is arranged to be loaded and discharged but thereafter means are provided to inhibit further retraction of the piston so as to prevent reloading of the syringe. Accordingly, drive rod 19 is formed with a pair of closely axially spaced ribs 19a therearound for capturing a spider element 21 therebetween. Spider element 21 is best shown in FIG. 29 and includes a plurality of radially and axially outwardly extending prongs 22. A cylindrical sleeve element 23 carried within the interior of barrel 11 slides with a limited degree of friction therealong. Sleeve element 23 has been disposed between the tips of prongs 22 and the side wall of barrel 11 whereby withdrawing rod 19 serves to cause spider 21 to be withdrawn as it moves together with sleeve 23. This outward movement continues until the upper edge 23a of sleeve element 23 engages a fixed stop in the form of a snap ring 24 carried in the outer end of syringe 10.

At that point, syringe 10 will have been substantially fully loaded, and by thrusting rod 19 forwardly into barrel 11 piston 17 serves to discharge the contents of syringe 10.

At this point, sleeve 23 is sufficiently frictionally engaged with the inner side wall of barrel 11 to be retained against forward movement as the tips of spider element 21 slide forwardly and freely therefrom. The prongs of spider element 21 are curved axially outwardly of syringe 10 and are of a sufficient length to extend into engagement with the side wall of barrel 11 after having slidably disengaged sleeve 23. After the contents have been fully discharged from syringe 10, the tips of prongs 22 will engage the inner side wall of barrel 11 to inhibit retracting drive rod 19 so as to prevent reloading of syringe 10.

Successive stages of operation of syringe 10 are shown in FIGS. 2, 3 and 4 as represented by the arrows 26, 27, 28, each of which is partially shown in dotted lines and partially shown as a solid arrow. Accordingly, in FIG. 2 plunger 17 is noted as commencing its withdrawal from the left-hand end of barrel 11. This rightward movement is substantially completed in FIG. 3 and in FIG. 4 it is evident that the plunger assembly has been withdrawn for purposes of loading the syringe and moved forwardly to disengage the tips of spider element 21 from sleeve 23 as plunger 17 moves toward its discharge end.

In the embodiment shown in FIGS. 1 through 4, the first figure of the series of figures is drawn in enlarged detail so as to accommodate the numbering thereon more effectively inasmuch as it will be readily evident that the same elements are associated in the subsequent FIGS. 2, 3 and 4. This same approach has been employed in conjunction with the subsequent embodiments now to be described.

According to another embodiment as shown in FIGS. 5 through 8 and FIG. 30, a syringe assembly 30 has been shown which includes a piston 31 coupled to the threaded end of a drive rod 33 which in turn carries a sleeve 32 therearound. A retaining unit 34 as shown best in FIG. 30 fixed in the axially outer end of barrel 37 by means of rivets 36 extending through the side wall of barrel 37 includes arcuately disposed prongs 38 sprung toward the axis of barrel 37. Accordingly, retaining unit 34 includes a cylindrical band 34a fixed within barrel 37 adjacent the axially outer end thereof. A plurality of curved prongs 38 are carried by band 34a to extend radially inwardly to cause the tips of prongs 38 to engage sleeve 32 in a manner restraining sleeve 32 against axially outward movement thereof while permitting rod 33 to be drawn outwardly therethrough for loading syringe 30.

Sleeve 32 is retained on rod 33 with sufficient friction whereby as rod 33 is driven forwardly sleeve 32 is carried with rod 33 and released from prongs 38 so as to travel with rod 33 during axially inward movement of the rod for discharging the contents of syringe 30. Prongs 38 thereby engage rod 33 after release of sleeve 32 and in a manner precluding axially outward movement of rod 33 thereby inhibiting reloading of the syringe.

According to another embodiment as shown in FIG. 9, a syringe 40 employs a coupling between the inner end of a drive rod 41 and a piston 42 whereby the coupling releases the inner end of rod 41 from piston 42 after the syringe has been loaded and discharged by movement of rod 41 and piston 42 between advanced and retracted positions and then between retracted and advanced positions.

By de-coupling piston 42 from rod 41, piston 42 cannot be again retracted.

As shown in detail in FIGS. 9 and 10 the inner end of drive rod 41 carries an enlarged portion thereon, such as the ball joint 43 threaded thereto. A ball socket 44 includes a threaded stud portion 46 threadedly engaged with a correspondingly threaded opening in the top of piston 42. Means for capturing ball joint 43 to be retained in ball socket 44 includes a plurality of radially outwardly sprung closure elements 47. As shown best in FIG. 10 the ball retainer unit 45 comprises a unitary structure including the closure elements 47, ball socket 44 and the threaded stud portion 46. In addition, ball retainer 45 carries a radially extending skirt 48 for purposes to be described further below.

As noted above, closure elements 47 are sprung radially outwardly whereby if not retained about ball joint 43, drive rod 41 becomes decoupled from piston 42.

Accordingly, means are provided for retaining elements 47 about ball joint 43, as now to be described.

A sliding element 49 slides along the inner side wall of the barrel of syringe 40. Element 49 comprises a funnel-shaped article having a collar portion 49a disposed to encircle and retain ball closure elements 47.

Accordingly, as thus arranged, moving rod 41 outwardly of the syringe moves piston 42 to its retracted position. As ball joint 43 remains retained within ball retainer 45 rod 41 serves to draw piston 42 to the right (as shown in FIG. 9). Sliding element 49 moves in response to contact between skirt 48 of retainer 45 and element 49. Accordingly, when skirt 48 is drawn into contact with the underside of the edge of the retaining collar 49a piston 42 can be retracted until the upper edge thereof makes contact with the underside of a fixed stop ring 51 mounted in the outer end of syringe 40.

Subsequently, upon moving piston 42 toward its advanced position, it will be readily evident that ball retainer 45 will move forwardly out of engagement with annular collar portion 49a and upon being so released the ball joint can continue to urge piston 42 to its advanced position. However, retraction of rod 41 draws retainer collar from elements 47 to release ball closure elements 47, whereby it will be evident that the rod will become decoupled from the piston.

The foregoing sequence of movements is believed to be best shown in FIGS. 11, 12 and 13 as represented by their associated arrows 52, 53, 54. In FIG. 13, ball 43 has been shown slightly retracted to demonstrate how it urges closure elements 47 apart to be released from ball retainer 45.

FIG. 10A shows a conical enlargement 143 carried on the end of rod 141. Enlargement 143 includes a conically shaped portion and a spherical portion 143a at the end. A retainer 145 formed with a peripheral skirt 148 therearound functions in a manner similar to retainer 45. However, the interior of retainer 145 defined by closure elements 147 includes a hollow conical region whereby the conical surface of the enlarged end 143 serves to wedge the closure elements 147 apart in response to withdrawing rod 141 after collar 149a has been removed. The threaded boss 146 couples retainer 145 to a piston 142.

Syringe 55 shown in FIGS. 14 through 19 represents another embodiment according to the invention. Accordingly, syringe 55 includes a barrel, piston, drive rod and fixed stop at the axially outer end of the barrel all in a manner comparable to previous embodiments noted above. Means for inhibiting the re-loading of syringe 55 includes a cylindrical sleeve member 56 formed with a beveled annular edge 56a for engaging the outer ends of a plurality of radially outwardly sprung prongs 57 carried by a spider element 58 in a manner serving to keep the pointed tips 64 of the prongs out of engagement with the inner side wall of the barrel.

Each prong 5, has been folded to include three panels 59, 60, 61 forming an integral element with increased rigidity. At the outer end of each prong 57, the center panel 60 has been shaped to include a point 64 protruding beyond the end edges 62, 63 of side panels 59, 61. End edges 62, 63 lie substantially in a common plane. Furthermore, edges 62, 63 are displaced sufficiently from point 64 whereby the inner side surface 156a of beveled edge 56a can engage both edges 62, 63 simultaneously while point 64 lies flush against the outer side surface 156b of beveled edge 56a. As thus disposed, tip 64 will remain disengaged from the inner side wall of the barrel of syringe 55. Spider element 58 is drawn against sleeve member 56 to cause prongs 57 to be held out of engagement with the side wall. Prongs 57 of spider element 58 (FIG. 19) are bent to extend radially and axially outwardly of drive rod 66. Accordingly, the prongs are sprung away from rod 56 when mounted thereon and have sufficient length to reach the inner sidewall surface of the barrel whenever released from engagement with beveled edge 56a.

Accordingly, sleeve member 56 serves to hold the pointed tips 64 of each prong clear of the side wall whenever the beveled edge 56a engages the outer end of prongs 57. Further, by disengaging the ends of prongs 57, the pointed tips 64 move into engagement with the inner side wall so as to inhibit subsequent retraction of the piston. If desired, spider element 58 as shown in FIG. 19 can employ three legs and function in substantially the same manner as the four legged element 58.

In addition, spider element 58 includes an annular hub 67 supporting the plurality of prongs 57. Hub 67 includes a peripheral opening 168 whereby the spider element can be snapped onto its associated drive rod. Drive rods 19, 66 preferably include a pair of axially spaced ribs 19a, 66a extending therearound and between which the spider element can be snapped onto the rod. The axial spacing between ribs 66a and 19a permits spider element 58 or 21 respectively to move slightly along drive rod 66 or 19 so as to allow slight retraction of the plunger if necessary.

Thus, syringe 55 can be charged with fluid by withdrawing drive rod 66 axially outwardly as shown being commenced in FIG. 14. As shown in FIG. 14, the beveled edge of sleeve member 56 serves to hold the pointed tips 64 out of engagement (or disengaged) from the side wall of the barrel of syringe 55 as shown best in FIG. 16. Accordingly, when syringe 55 has been fully charged, sleeve member 56 strikes a fixed stop in the form of the snap ring 51 retained in the axially outer end of the barrel of syringe 55. Subsequently, by urging rod 66 inwardly of syringe 55 fluid material discharges while the outer ends of prongs 57 remain released from the beveled edge of sleeve member 56. There is sufficient friction between the inner side wall of syringe 55 and the outer cylindrical surface of member 56 so that it will be retained in the axially outermost position as rod 66 is urged forwardly into the syringe. In this way as prongs 57 move away from member 56 the resilient radially outward urging of the prongs causes their tips 64 to engage the inner side wall of the syringe. Any attempt to withdraw the piston will be resisted by engagement of the spider element with the inner side wall of the syringe.

As noted above, the various stages of operation of the syringe as shown in FIG. 14, 15, 16 and 17 are represented by an associated arrow 68, 69, 71, 72, respectively, having portions which are in dotted lines and portions which are solid whereby the solid line portions indicate the amount of movement of the piston which has been achieved and the dotted portions represent the amount of movement remaining.

According to yet a further embodiment as shown in FIGS. 20 through 28 a non-reusable syringe 70 has been shown wherein the means for inhibiting multiple retractions of the piston includes a drive rod assembly 73 shaped to include a relatively wide body formed with a first series of tapered teeth extending radially and axially outwardly therealong. A second series of tapered teeth 76 is disposed above the first series 74 and inclined axially inwardly and radially outwardly along the rod assembly 73.

Detent means carried within the barrel of syringe 70 and movable into and out of engagement with the first series of teeth 74 has been spaced from the first series of tapered teeth 74. Thus, a pair of flexible plastic dog elements 77 of a generally planar construction include a mounting piece portion 77a connected to the main body of dog element 77 via a narrow neck 77b forming a flexible hinge to element 77. Dog elements 77 are retained within a barrel of syringe 70 by means of plastic rivets 78 extending through the side wall of the barrel.

Each dog element 77 carries a spring-like finger 79 interposed between the interior wall of the barrel of syringe 70 and the backside of dog element 77 for urging dog element 77 toward rod assembly 73. The confronting edge of dog element 77 has been formed to include a series of teeth 81 forming detent means for movement into and out of engagement with the first series of teeth 74. It will be readily evident that when teeth 81 engage teeth 74, rod assembly 73 cannot be withdrawn for loading of syringe 70.

However, in order to permit rod assembly 73 to be withdrawn for an initial loading of the syringe and thereafter prevent it from being loaded, spacer means have been interposed between the second series of tapered teeth 76 and dog element 77. A spacer has been provided between dog element 77 and teeth 76. The spacer is removable in response to retraction of rod assembly 73 whereby, when inserted, teeth 81 of dog element 77 remain out of engagement with their associated teeth 74 until removal of the spacer means.

More particularly, the spacer means is best shown in FIGS. 24, 25 and 26 wherein the leading end of dog element 77 carries a support element 82 pivoted in a slot 83 formed in the axially inner end thereof.

Support elements 82 include teeth 84 formed to cooperate with teeth 76. It is to be observed that teeth 76 are oriented in an opposite direction to those of teeth 74 whereby teeth 76 are tapered to protrude radially outwardly within the barrel of syringe 70 as well as to be inclined axially inwardly.

Supported element 82 for spacing teeth 81 from engagement with teeth 74 initially is disposed tucked between element 77 and teeth 76 as shown in FIG. 20, 25 and 26. In this position it will be readily evident that teeth 84 are arranged to ride over teeth 76 as drive rod assembly 73 is urged inwardly of syringe 70. As thus arranged, the piston can be moved substantially fully inwardly of syringe 70 to permit loading thereof.

It is to be observed that the orientation of teeth 76 with respect to teeth 84 of support member 82 is such that support member 82 will ride over teeth 76 as the piston is drawn outwardly when loading syringe 70. Thus, during loading teeth 74 are maintained out of contact with teeth 81 of dog elements 77. When discharging the contents of syringe 70, however, the initial forward movement of drive rod assembly 73 serves to cause teeth 76 to engage teeth 84 of support element 82 and thereby force it forwardly and outwardly from between dog element 77 and drive rod assembly 73. The orientation of teeth 81 and 74 is such that teeth 74 simply lift dog elements 77 away from rod assembly 73 as rod assembly 73 is moved forwardly but will prevent subsequent retraction of rod assembly 73 with regard to dog elements 77.

Accordingly, it is readily evident that the arrangement shown in FIGS. 20 through 28 provides something of a double-acting ratchet arrangement wherein a first series of teeth are oriented to positively engage when the drive rod is moved in one direction and a second series of teeth are provided to positively engage when the rod is moved in its opposite direction.

As thus arranged, spacing means can be carried by the dog elements 77 to ride over a first series of teeth such as 76 as the syringe is being loaded and in response to discharging the contents thereof the spacing is removed without inhibiting the further advance of the piston in the syringe in view of the fact that teeth 74 simply ride underneath the teeth 81 of dog elements 77 as the syringe is being discharged. However, by removing support member 82 from between teeth 76 and dog elements 77 teeth 81 now lie in positive engagement with teeth 74 whereby retraction of the piston will not be permitted.

The foregoing function of support element 82 is best shown in the sequence of FIGS. 21, 22, 23 wherein support element 22 is shown in FIG. 21 as permitting the drive rod assembly 73 to be withdrawn by maintaining spacing between teeth 74 and 81. Also, as noted by the arrow 86 associated with FIG. 22 the piston has been substantially fully withdrawn whereby in FIG. 23 the piston has been thrust forwardly to discharge the contents of the syringe thereby moving the support elements 82 forwardly and outwardly under the action of teeth 76.

However, notwithstanding the fact that teeth 81 of dog elements 77 engage teeth 74 of rod assembly 73 virtually immediately after the rod assembly moves forwardly the orientation of the inclination of teeth 74 is such with respect to teeth 81 that they will readily pass beneath teeth 81 in the manner of the forward movement of a ratchet, i.e., teeth 81 will ride over teeth 74 as rod assembly 73 moves into syringe 70.

From the foregoing it will be readily evident that there has been provided a non-reusable syringe of a type which can be loaded and discharged but thereafter not reloaded.

I claim:

1. A non-reloadable syringe capable of being charged and discharged only once comprising an elongate right cylindrical barrel, a small opening at one end of said barrel and means for supporting a hypodermic needle at said one end in fluid communication with said opening, a plunger assembly disposed within said barrel for movement between advanced and retracted positions therealong to load said syringe, said positions being defined by the internal extremities of said barrel, respectively the needle end and the other end thereof, said plunger assembly including a piston fitted snugly within said barrel and a drive rod carried axially of said barrel from said piston to protrude from said barrel at the other end thereof, said rod serving to retract said piston outwardly of said barrel for loading same from the extremity at the needle end thereof and to urge said piston inwardly thereof to discharge the contents therefrom, means for inhibiting further retraction of said piston to prevent reloading of the syringe, and the interior side wall of said barrel being continuously smooth from said one end to the other.

2. A non-reloadable syringe capable of being charged and discharged only once comprising an elongate cylindrical barrel, a small opening at one end of said barrel and means for supporting a hypodermic needle at said one end in fluid communication with said opening, a plunger assembly disposed within said barrel for movement between advanced and retracted positions therealong said assembly including a piston fitted snugly within said barrel and a drive rod carried axially of said barrel from said piston to protrude from said barrel at the other end thereof, said rod serving to retract said piston outwardly of said barrel for loading same and to urge said piston inwardly thereof to discharge the contents therefrom, means for inhibiting further retraction of said piston to prevent reloading of the syringe in which the last-named means comprises a spider element having a plurality of radially extending prongs formed to include a point at one end thereof, said spider element being carried on said rod with said prongs inclined axially outwardly from and radially of said rod, said prongs being sprung radially away from said rod, said prongs extending sufficiently to engage the inner wall surface of said barrel, and a sliding sleeve element within said barrel disposed to hold the ends of said prongs disengaged from said barrel while said sleeve element and spider move together axially outwardly along said barrel in response to axial retraction of said plunger assembly, and a fixed stop carried by said barrel for engaging and arresting said sleeve element, said prongs being disposed to readily disengage said sleeve element in response to movement of said plunger assembly into said barrel to discharge material therefrom via said small opening and thereafter serving to engage the inner surface of said barrel to inhibit retraction of said rod.

3. In a syringe of a type to be charged with fluid material and for discharging said material via a given end of the syringe, said syringe comprising first and second members disposed in coaxially spaced relation to each other, a first of said first and second members being axially movable relative to the other between advanced and retracted positions for loading and discharging the syringe, sliding means axially movable with respect to a given one of said first and second members, a plurality of pointed prongs carried by the other one of said first and second members, said sliding means serving to maintain said prongs disengaged from said given one of said members during retraction of said first of said members, said prongs being disengagable from said sliding means for engagement of said prongs with said other one of said members in response to movement of said first of said members to its advanced position for discharging fluid material from said syringe, engagement of said prongs with said other one of said members serving to inhibit retraction of said first of said members.

4. A non-reloadable syringe according to claim 3 in which said first and second members respectively comprise an elongate cylindrical barrel and a plunger assembly including a drive rod and piston disposed within said barrel, and in which said sliding means comprises a sleeve carried on and slidable with respect to said rod, a cylindrical band fixed within said barrel adjacent the axially outer end thereof, a plurality of curved prongs carried by said band to extend radially inwardly to cause the tips of said prongs to engage said sleeve in a manner restraining said sleeve against axially outward movement thereof while permitting said rod to be drawn outwardly therethrough for loading said syringe, said prongs being oriented in a manner and said sleeve having a sufficient grip on said rod to cause said sleeve to be released from said prongs to travel with said rod during axially inward movement of said rod for discharging the contents of said syringe, said prongs engaging said rod after release of said sleeve and in a manner precluding axially outward movement of said rod thereby inhibiting reloading the syringe.

5. A syringe according to claim 1 in which the last named means comprises a coupling interposed between the inner end of said rod and said piston, said coupling serving to retain an end of said rod to said piston during a first retraction thereof for loading the barrel with a predetermined dose of fluid material, said coupling serving to continue to engage said piston during discharge of the contents of the syringe, said coupling having means serving to release said rod from said piston in response to a subsequent retraction of said rod.

6. A non-reloadable syringe capable of being charged and discharged only once comprising an elongate cylindrical barrel, a small opening at one end of said barrel and means for supporting a hypodermic needle at said one end in fluid communication with said opening, a plunger assembly disposed within said barrel for movement between advanced and retracted positions therealong said assembly including a piston fitted snugly within said barrel and a drive rod carried axially of said barrel from said piston to protrude from said barrel at the other end thereof, said rod serving to retract said piston outwardly of said barrel for loading same and to urge said piston inwardly thereof to discharge the contents therefrom, means for inhibiting further retraction of said piston to prevent reloading of the syringe in which the last named means includes a drive rod shaped to include a wide body formed with a first series of tapered teeth inclined and extending radially and axially outwardly therealong, a second series of tapered teeth disposed to extend above said first series and inclined axially inwardly and radially outwardly along said rod, detent means carried within said barrel and movable into and out of engagement with said first series of teeth, spacer means interposed between said second series of tapered teeth and said detent means to maintain said detent means spaced from said first series of teeth, said spacer means being pivotally mounted to said detent means and formed to include teeth for engaging said second series of teeth, said spacer serving to disengage said first series of teeth from said detent means and to engage said second series of teeth as said rod is moved into said barrel, said spacer being thereby moved out of a position between said detent means and said second series of teeth so as to lower said detent means to ride on said first series of teeth in a manner preventing retraction of said rod while permitting forward movement thereof.

7. A non-reloadable syringe capable of being charged and discharged only once comprising an elongate cylindrical barrel, a small opening at one end of said barrel and means for supporting a hypodermic needle at said one end in fluid communication with said opening, a plunger assembly disposed within said barrel for movement between advanced and retracted positions therealong said assembly including a piston fitted snugly within said barrel and a drive rod carried axially of said barrel from said piston to protrude from said barrel at the other end thereof, said rod serving to retract said piston outwardly of said barrel for loading same and to urge said piston inwardly thereof to discharge the contents therefrom, means for inhibiting further retraction of said piston to prevent reloading of the syringe, the last named means comprising a coupling interposed between the inner end of said rod and said piston, said coupling serving to retain an end of said rod to said piston during a first retraction thereof for loading the barrel with fluid material, said coupling serving to continue to engage said piston during discharge of the contents of the syringe, said coupling having means serving to release said rod from said piston in response to a subsequent retraction of said rod.

* * * * *